(12) United States Patent
Lafont et al.

(10) Patent No.: US 8,119,122 B2
(45) Date of Patent: Feb. 21, 2012

(54) USE OF GINGIVAL FIBROBLASTS FOR VASCULAR CELL THERAPY

(75) Inventors: Antoine Lafont, Paris (FR); Bruno Gogly, Hondevilliers (FR)

(73) Assignees: Universite Paris Decartes, Paris (FR); L'Assistance Publique-Hopitaux De Paris, Paris (FR)

( * ) Notice: Subject to any disclaimer, the term of this patent is extended or adjusted under 35 U.S.C. 154(b) by 1114 days.

(21) Appl. No.: 11/571,542

(22) PCT Filed: Jul. 1, 2005

(86) PCT No.: PCT/FR2005/001690
§ 371 (c)(1),
(2), (4) Date: Aug. 9, 2007

(87) PCT Pub. No.: WO2006/013261
PCT Pub. Date: Feb. 9, 2006

(65) Prior Publication Data
US 2008/0025954 A1    Jan. 31, 2008

(30) Foreign Application Priority Data
Jul. 2, 2004 (FR) .................................. 04 07357

(51) Int. Cl.
*C12N 5/02* (2006.01)

(52) U.S. Cl. ..................................... 424/93.7

(58) Field of Classification Search ........................ None
See application file for complete search history.

(56) References Cited

U.S. PATENT DOCUMENTS 5,885,829 A    3/1999    Mooney et al.

FOREIGN PATENT DOCUMENTS

| EP | 0 393 788 A | 10/1990 |
| WO | WO 98/22154 A | 5/1998 |
| WO | WO 99/51164 A | 10/1999 |
| WO | WO 01/82773 A | 11/2001 |

OTHER PUBLICATIONS

Losy et al, J Vasc Surg (Jun. 2003), vol. 37, No. 6, pp. 1301-1309.*
Allaire et al, J Clin Invest (1998), vol. 102, pp. 1413-1420.*
Hallett JW, "Aortic Dissection" (2008) The Merck Manual for Healthcare Professionals. Whitehouse Station, NJ: Merck & Co, Inc. URL: <http://www.merck.com/mmpe/sec07/ch079/ch079c.html?qt=aortic dissection&alt=sh> accessed Aug. 13, 2010.*
Lam JYT, "Atherosclerosis" (2008) The Merck Manual for Healthcare Professionals. Whitehouse Station, NJ: Merck & Co, Inc. URL: <http://www.merck.com/mmpe/sec07/ch072/ch072b.html?qt=atherosclerosis&alt=sh> accessed Aug. 13, 2010.*

* cited by examiner

*Primary Examiner* — Allison Ford
(74) *Attorney, Agent, or Firm* — Alston & Bird LLP

(57) ABSTRACT

The invention relates to the use of gingival fibroblasts for obtaining a cellular composition for treating arterial-remodelling pathology, for example an aneurysm, post-cryoplasty stenosis and restenosis, an aortic dissection or atherosclerosis.

6 Claims, 15 Drawing Sheets

USE OF GINGIVAL FIBROBLASTS FOR VASCULAR CELL THERAPY

BACKGROUND OF THE INVENTION

The present invention relates to the use of gingival fibroblasts in vascular cell therapy, in particular for the treatment of arterial pathologies.

The arterial wall consists of three superimposed layers called tunicae. The inner tunica (intimae) consists of a layer of endothelial cells. The intermediate tunica (media) consists mainly of smooth muscle fibers and connective tissue rich in elastic fibers. The outer tunica (adventica) is a connective envelope that surrounds the whole assembly.

Arteries are subjected to numerous attacks of various origin (hypoxia, lipid overload, hemodynamic forces, atheroma, hypertension, etc.) that can induce arterial wall lesions. During the repair of these lesions, an abnormal healing reaction can occur, resulting from an imbalance between degradation and synthesis of the extracellular matrix, and inducing pathological arterial remodeling, which can be reflected by a vascular enlargement (aneurism) or, on the other hand, by a constriction (stenosis, occurring secondarily during atherogenesis, or restenosis, subsequent in particular to an angioplasty, evolving in the course of cicatricial remodeling toward the reappearance of a stenosis).

For example, in aneurismal lesions, enzymatic degradation of the extracellular matrix components, in particular of the elastic fibers, and a decrease in the number of smooth muscle cells (SMCs) are observed in the media; a fibrosis accompanied by considerable inflammatory infiltration is observed in the adventica.

The degradation of the extracellular matrix components involves various matrix proteases. Among these, mention may in particular be made of an elastase, matrix metalloproteinase-9 (MMP9) synthesized by the infiltrated leukocytes and the physiological host cells (endothelial cells, smooth muscle cells and adventitial fibroblasts), and which is in large part responsible for the elastic fiber fragmentation (THOMPSON, J. Clin. Invest. 96: 318-326, 1995). In parallel, the increased sparcity of the SMCs in the media leads to a decrease in the synthesis of the extracellular matrix components, and in that of matrix protease inhibitors, which are mainly synthesized by these SMCs (LOPEZ-CANDALES et al., Am. J. Pathol. 150: 993-1007, 1997).

In the case of stenosis and of restenosis a retractile fibrous remodeling occurs, which can also be considered to be an abnormal wound healing process. This remodeling is characterized by intimal fibrous hyperplasia (LAFONT et al., Circ. Res. 76(6): 996-1002, 1995), and appears to be related to an increase in collagen in the neointima, in the media and in the adventica (LAFONT et al., Circulation 100(10): 1109-1115, 1999; DURAND et al., Arch. Mal. Coeur Vaiss. 94(6): 605-611, 2001).

At the current time, the treatment of arterial pathologies is mainly based on surgery and cardiology procedures (vascular surgery, aortocoronary and peripheral bypasses, aortic dacron prostheses, coronary and peripheral artery angioplasty, aortic endoprostheses, etc.). However, these invasive techniques do not treat the cause, but the consequences of the pathology. They make it possible to improve the patient's situation without being able to curb the development of the disease.

It therefore appears to be necessary to have new means of treatment that are less invasive and that make it possible to effectively treat the pathological arterial remodeling.

ALLAIRE et al. (J. Clin. Invest. 102(7): 1413-1420, 1998) have observed, in an experimental aneurism model in rats, that local implantation of SMCs in the arterial wall induces an inhibition of elastic fiber degradation and of the formation of an aneurism. It has also been shown, in rats, that already formed experimental aneurisms can be stabilized by the local injection of SMCs. This stabilization is associated with secretion of TGFβ of paracrine origin at the level of the cell transplant (LOSY et al., J. Vasc. Surg. 37(6): 1301-1309, 2003).

However, a major obstacle to the use of SMCs for the treatment of aneurisms by cell therapy comes from the need to obtain these SMCs from stem cells. The stem cells used come from the marrow or the blood and are very difficult to obtain.

SUMMARY OF THE INVENTION

The inventors undertook to investigate whether cell types other than arterial wall SMCs could possible be used in cell therapy, and had the idea of testing gingival fibroblasts.

Gingival fibroblasts are mesenchymal cells capable of migrating, adhering and proliferating in the soft connective tissues of the gum, thus maintaining the integrity of the gingival tissue subjected to numerous attacks such as mechanical forces, bacterial infections, variations in pH, in temperature, etc. (GOGLY et al., Clin. Oral Invest. 1: 147-152, 1997; GOGLY et al., Biochem. Pharmacol. 56(11): 1447-1454, 1998; EJEIL et al., J. Periodontol. 74(2): 188-195, 2003).

Depending on the environmental conditions to which they are subjected, gingival fibroblasts are capable of changing phenotype and of responding to stimuli from the gingival tissue environment through proliferation, migration, or synthesis or degradation of extracellular matrix components.

They are thus capable of synthesizing various extracellular matrix components: collagens (types I, III, V, VI, VII, XII), elastic fibers, proteoglycans and glycosaminoglycans, and glycoproteins. They can also produce a variety of enzymes (in particular metalloproteases) capable of degrading these macromolecular components. Finally, they can also express tissue inhibitors of metalloproteases, which inhibit the active forms of MMPs.

The inventors have carried out cocultures of gingival fibroblasts and SMCs, and have observed that the interactions between these cells result in the inhibition, by the gingival fibroblasts, of the MMP9 activity by the SMCs, and also in the potentiation of the secretion of TGFβ by the two cell types. These effects are specific for gingival fibroblasts, and are not observed when the SMCs are cocultured with dermal or adventitial fibroblasts.

Identical observations have also been made in cocultures of gingival fibroblasts and lesioned arteries. This organotypic model has also made it possible to show that the presence of gingival fibroblasts induces a protection of the elastic network.

It therefore appears that gingival fibroblasts have, firstly, an inhibitory effect on one of the main factors of aneurism formation, i.e. MMP9 responsible for the degradation of the elastic network, and, secondly, an activating effect on a factor that is favorable to the stabilization of aneurisms, i.e. the secretion of TGFβ.

The inventors have also carried out, in rabbits, in vivo trials consisting of transplantation of gingival fibroblasts obtained from a sample of gingival tissue from a rabbit, into the arterial wall of said rabbit and have noted that these autologous gingival fibroblasts are capable of becoming inserted in the wall, at the level of the media.

A subject of the present invention is therefore the use of gingival fibroblasts for obtaining a cell composition for use in the treatment of a pathology consisting of the remodeling of a nonmineralized connective tissue other than gingival tissue, in particular of an arterial-remodeling pathology.

The gingival fibroblasts can be used, in accordance with the invention, in all vascular pathologies, in particular arterial pathologies, with profound extracellular matrix impairments. Mention will in particular be made of: atherosclerosis, vulnerable plaque, restenosis, arterial aneurisms, aortic dissection. Outside the vascular field, gingival fibroblasts could also modulate tissue remodeling in pathologies involving extracellular matrix impairments: cutaneous wound healing, tissue repair (patients with burns, cancer, substance loss).

According to a preferred embodiment of the present invention, said pathology is an aneurism.

According to another preferred embodiment of the present invention, said pathology is a post-angioplasty stenosis or restenosis.

Said fibroblasts are preferably autologous fibroblasts, i.e. fibroblasts derived from gingival tissue taken beforehand from the individual for whom the treatment is intended, and placed in culture. Preferably, these fibroblasts are cultured for at least 14 days, and advantageously for 14 to 70 days.

BRIEF DESCRIPTION OF THE DRAWINGS

FIGS. 20A, 20C, and 20E depict the artery cultured alone at days 3, 7, and 21, respectively. FIGS. 20B, 20D, and 20F depict the artery cocultured with gingival fibroblasts at days 3, 7, and 21, respectively.

FIG. 21A depicts sections of a normal rabbit artery model at 10× and 40× magnification. FIG. 21B depicts a section of an aneurism rabbit artery model at 5× magnification.

DETAILED DESCRIPTION

Cultures of gingival fibroblasts that can be used for implementing the present invention can be obtained by conventional techniques, which are known in themselves to those skilled in the art (BARLOVATZ-MEIMON et al., "culture de cellules animales" ["Animal cell culture"] p. 898, ill. Paris: INSERM, 2003).

The implantation of the fibroblasts in the arterial wall can be carried out in various ways: either locally by injection using balloon catheters equipped with microneedles (INFILTRATOR), the injection being via the external or internal route into the adventica or the periadventitial tissue, or via the general route (peripheral venous or arterial route upstream of the site of injection with targeting carried out by magnetic guidance (prior intracellular incorporation of superparamagnetic nanoparticles)), or the biological route (WILHEM et al., Eur. Biophys. J. 31(2): 118-125, 2002; PANYAM et al., J. Drug Target 10(6): 515-523, 2002).

It is also possible, if desired, to combine with the gingival fibroblasts products that are involved in matrix remodeling, for example decorin (proteoglycan involved in matrix remodeling) (AL HAJ ZEN et al., Matrix Biol. 22(3): 251-258, 2003) or hyaluronic acid.

The present invention will be understood more clearly from the further description which follows, which refers to nonlimiting examples illustrating the effects of the gingival fibroblasts that can be used in vascular cell therapy.

EXAMPLE 1

Secretion of MMP2, MMP9, TIMP-1 and TGFβ in Cocultures of Gingival Fibroblasts and Smooth Muscle Cells Labeling of Fibroblasts The gingival fibroblasts are labeled with anionic nanoparticles of maghemite as described by WILHEM et al. (Biomaterials 24: 1001-1011, 2003).

The gingival fibroblasts (six different cultures) are cultured to confluence in 10% fetal calf serum (FCS); and, after 48 h, the culture supernatant is removed and the cells are cultured in serum-free medium.

Figure 1:
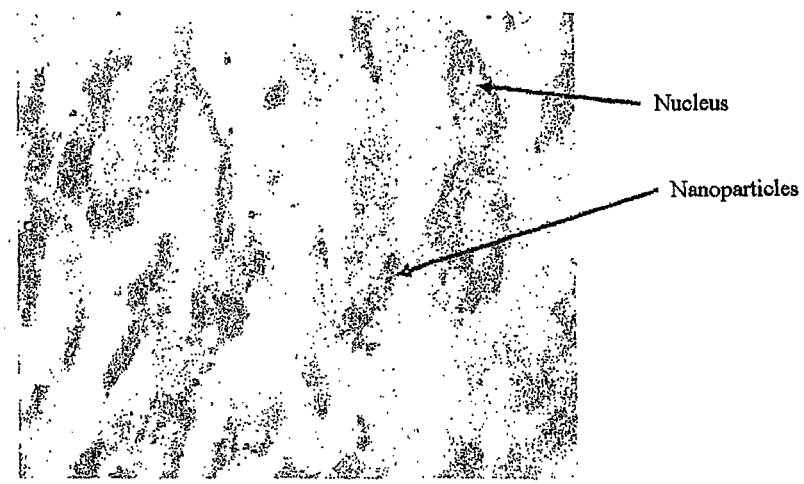
FIG. 1 depicts gingival fibroblasts labeled with anionic nanoparticles.

The quality of gingival fibroblast labeling with these nanoparticles is controlled by Perl staining (Prussian blue). The nanoparticles are absorbed and internalized into the endosome of the gingival fibroblasts, as shown in FIG. 1.

In order to verify that the labeling does not modify the phenotype of the gingival fibroblasts, the effect of the incorporation of the nanoparticles on the secretion of matrix metalloproteinase-2 (MMP2) and of cytokines IL-1β and TGFβ was evaluated at D1, D3 and D5 (days of culture).

An increase in the production of MMP2 and of IL-1β is observed in the labeled fibroblasts at D1, and said production returns to the normal level at D3 and D5. This transient increase is probably due to the stress following the incorporation of nanoparticles. On the other hand, no modification of the production of TGFβ is observed during the period studied.

Cocultures of Gingival Fibroblasts and Smooth Muscle Cells

Cocultures of labeled gingival fibroblasts (FGs) and smooth muscle cells (SMCs) are carried out in collagen gels according to the method described by GILLERY et al. (Experinetia 45(1): 98-101, 1989).

In brief, the cells are obtained from gingival samples for the gingival fibroblasts, and from the arterial media for the smooth muscle cells. The samples (gum and arterial media) are placed in primary culture in Petri dishes in DMEM medium/20% FCS. At confluence, the cells are trypsinized and placed in culture again in a DMEM medium/10% FCS. After several passages in this medium, the cells are cultured in collagen I (60 000 cells in 2 ml of collagen) for 3, 7, 14 or 21 days. The culture media (DMEM/10% FCS) in which the gels bathe are changed every week.

Gingival fibroblast cultures and smooth muscle cell cultures are carried out separately, as a control, under the same conditions.

MMP9 Secretion by the SMCs

The MMP9 secretion is located by immunodetection at D3, and observed by optical microscopy (×160).

MMP9 is not detected in the fibroblasts: it is detected only at the sites corresponding to the location of the SMCs in the gel. These results corroborate previous studies according to which fibroblasts do not express MMP9 (GOGLY et al., 1998, mentioned above).

Effects of FG/SMC Interactions on the Activity of MMP2 and of MMP9 and on the Transcription of MMP9

Figure 2:
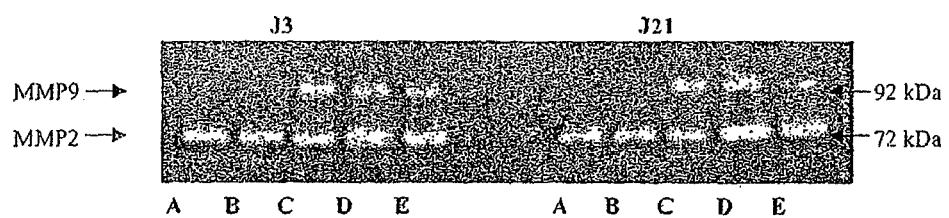
FIG. 2 depicts the activity of MMP9 and MMP2 as determined by zymography of samples of FG and/or SMC containing cell cultures.

Evaluation of the Activity of MMP9 and of MMP2 by Zymography 20 μl of a sample of a culture of FGs and/or of SMCs are diluted to ½ in 1M Tris at pH 6.8 containing 50% of glycerol and 0.4% of bromophenol blue, and then subjected to electrophoresis in an SDS 10% polyacrylamide gel containing 1 mg/ml of α-casein (Sigma Chemical) for 1hour. The gels are washed in 2.5% Triton X-100 diluted in distilled water, and then incubated in 100 mM Tris-HCl, 5 mM $CaCl_2$, 0.005% Brij-35, 0.001% $NaN_3$, at pH 7.4, for 36hours, at 37° C. The gels are then stained with 0.25% Coomassie blue (Biorad, ref. G 250) (50% methanol, 10% acetic acid) and then destained appropriately (40% ethanol, 10% acetic acid). The results are presented in FIG. 2.

A: MMP2 activity for 600 nonlabeled fibroblasts (control);
B: MMP2 activity for 600 labeled fibroblasts cultured in a collagen gel;
C: MMP2 and MMP9 activities for 600 SMCs cultured in a collagen gel;
D: MMP2 and MMP9 activities for 600 cultured labeled fibroblasts+600 SMCs cultured separately in a collagen gel (the media of the 2 separate cultures are added in order to determine the total activity in the absence of interactions between the two cell types);
E: MMP2 and MMP9 activities for 600 labeled fibroblasts and 60 000 SMCs cocultured in a collagen gel.

The results show that the gingival fibroblasts in culture do not express MMP9 (A and B), unlike the SMCs (C and D). On the other hand, the fibroblasts inhibit the activity of MMP9 secreted by the SMCs in coculture (E). The same results are observed at D3 and D21. As regards MMP2, a decrease in activities is observed in the cocultures (E) compared with that which could theoretically be expected (D). This decrease is, however, less significant than that of MMP9.

Evaluation of MMP9 Transcription by RT PCR

Figure 3:
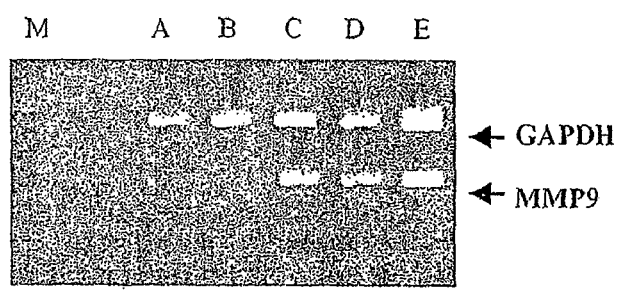
FIG. 3 depicts expression of MMP9 mRNA in FG and SMC cell cultures, as determined by RT-PCR using MMP9 primers followed by resolution on a 2% agarose gel.

The total RNA (1 or 2 μg) is extracted from the cultures or from the cocultures of FGs and of SMCs at D14, using the MMP-CytoXpress Multiplex PCR kit (BioSource International). The mRNAs obtained are reverse-transcribed using a reverse transcriptase, and then a PCR is carried out using MMP9-specific primers, as follows: a denaturation step at 95° C. for 1 min, 5 cycles of denaturation at 94° C. for 1 min and hybridization at 60° C. for 4 min, 35-40 cycles of denaturation at 94° C. for 1 min and hybridization at 68° C. for 2.5 min, and a final step at 70° C. for 10 min followed by cooling to 20° C. GAPDH, which is transcribed constitutively, is used as control. The PCR products obtained are subjected to 2% agarose gel electrophoresis. The gel is examined under UV and photographed. The results are presented in FIG. 3.

M: DNA molecular weight marker;
A: culture of nonlabeled FGs (1 μg RNA);
B: culture of labeled FGs (1 μg RNA);
C: culture of SMCs (1 μg RNA);
D: coculture of SMCs and FGs (1 μg RNA);
E: coculture of SMCs and FGs (2 μg RNA).

The results show no transcriptional modification of MMP9 in the cultures of SMCs (C) and the cocultures of SMCs and FGs (D and E), whereas a decrease in the activity of this enzyme in said cocultures was previously demonstrated by zymography. Consequently, the action of the gingival fibroblasts lies at the translational or post-translational level.

Effects of FG/SMC Interactions on the Production of TIMP-1

The MMP9 inhibitor (TIMP-1) is expressed by the gingival fibroblasts and inhibits the active form of MMP9 by forming an inactive MMP9/TIMP-1 complex.

The cell interactions are studied through the expression of TIMP-1 at D3, D7, D14 and D21 (days of culture).

Evaluation of the Production of TIMP-1 by Dot-Blot

Aliquots (1 ml) of supernatant of a coculture of FGs and SMCs in the collagen gel are brought to a final volume of 100 μl in DMEM medium and centrifuged at 10 000 g in order to remove the cell debris, and then 10 μl of a solution of 1 M Tris-HCl, 150 mM NaCl, pH 7.5 are added. As a control, culture supernatants from FGs alone or from SMCs alone are prepared under the same conditions. The samples (5 μl) are deposited in triplicate on a nitrocellulose membrane (Biorad, ref. 1 620 115). The membranes are incubated with 1% blocking solution (Boehringer, ref. 1 096 176) for 1 hour at ambient temperature, and then rinsed 4×15 min in TBS-Tween (50 mM Tris, 150 mM NaCl, 0.1% Tween 20, pH 7.5). The membranes are the incubated with a goat anti-human anti-TIMP-1 polyclonal primary antibody (1/500, R&D Systems, ref. AF970), overnight at ambient temperature. The primary antibody specific for the free forms of TIMP-1. After washing in TBS-Tween (4×15 min), the blots are incubated with a peroxidase-labeled secondary antibody (1/1000) for 1 hour, then deposited in a developing solution containing hydrogen peroxide and diacylhydrazide (Luminol, Boehringer, ref. 1 500 694) for 1 min, and then brought into contact with a Kodak BIOMAX MR photographic film for a period ranging from several seconds to 10 min. The film is then developed and fixed. The multiple exposures are examined in order to confirm the linearity of the results. The results are presented in FIG. 4A.

Figure 4A:
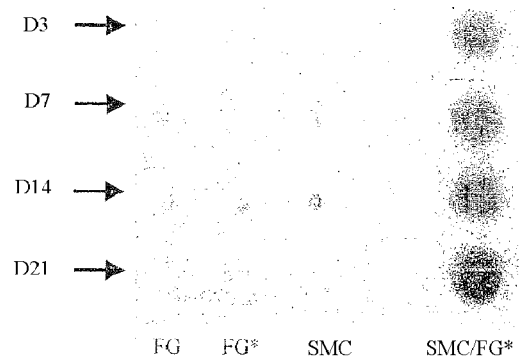
FIG. 4A depicts the secretion of TIMP-1 protein in the supernatant of FG and/or SMC cell cultures, as determined by an immunoblot assay. Quantification of the results shown in FIG. 4A is presented in FIG. 4B.

Legend of FIG. 4A:
FG=culture of $10^5$ nonlabeled FGs;
FG*=culture of $10^5$ labeled FGs;
SMC=culture of $10^5$ SMCs;
SMC/FG*=coculture of $10^5$ labeled FGs and $10^5$ SMCS.

The image of the film is transmitted to a computer using a video camera. The software (Imagenia 3000, station BIO-COM 200) evaluates, firstly, the density of the spots developed on the membranes and, secondly, their surface area in a semi-automatic manner by definition of the outline. The results are presented in FIG. 4B.

Figure 4B:
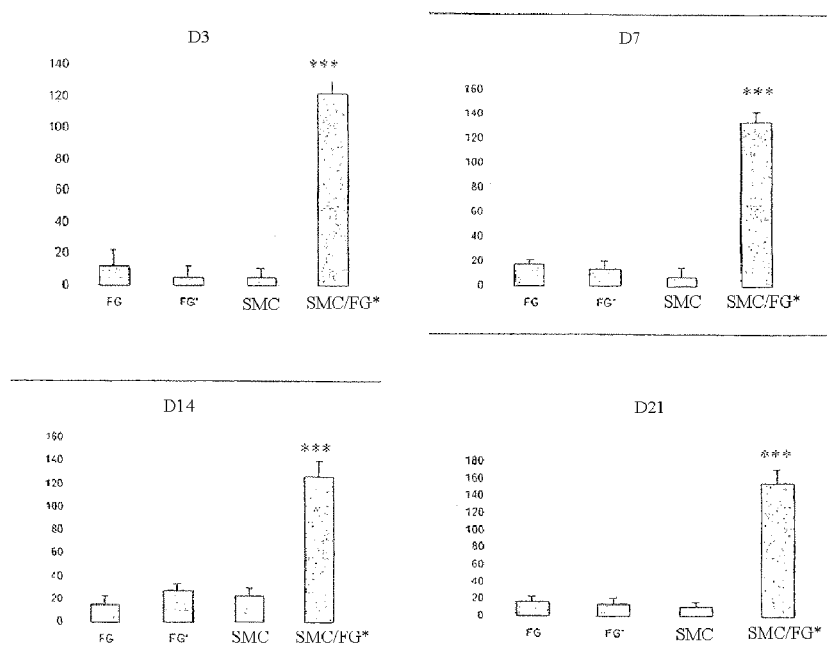

Legend of FIG. 4B:
X-axis
FG=culture of $10^5$ nonlabeled FGs;
FG*=culture of $10^5$ labeled FGs;
SMC=culture of $10^5$ SMCs;
SMC/FG*=coculture of $10^5$ labeled FGs and $10^5$ SMCs.
Y-axis=secretion of TIMP-1 (pg/ml/$10^5$ cells)
***=Fischer Student's T test p<0.001

The results show a large increase in TIMP-1 secretion in the cocultures of FGs and SMCs, in comparison with TIMP-1 secretion in the cultures of FGs alone or SMCs alone. The same results are observed at D3, D7, D14 and D21.

Evaluation of TIMP-1 Transcription by RT PCR

Figure 5:
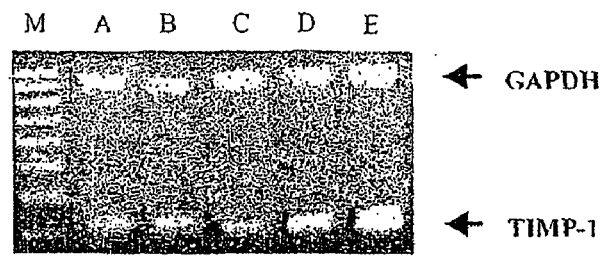
FIG. 5 depicts expression of TIMP-1 mRNA in FG and/or SMC cell cultures, as determined by RT-PCR using TIMP-1 primers followed by resolution on a 2% agarose gel.

The TIMP-1 mRNA extraction and RT PCR are carried out as described above for MMP9, using TIMP-1-specific primers. The results are presented in FIG. 5.
M: DNA molecular weight marker;
A: culture of nonlabeled FGs (1 µg RNA);
B: culture of labeled FGs (1 µg RNA);
C: culture of SMCs (1 µg RNA);
D: coculture of SMCs and FGs (1 µg RNA);
E: coculture of SMCs and FGs (2 µg RNA).

The results show an increase in TIMP-1 transcription in the cocultures of SMCs and FGs (FIG. 5, D and E), which correlates with the increase in the TIMP-1 secretion (FIG. 4).

Evaluation of the Production of MMP9/TIMP-1 Complexes by ELISA Assay

The cell interactions are studied through the production of MMP9/TIMP-1 complexes at D3, D7, D14 and D21 (days of culture), by ELISA assay using a DuoSet® ELISA Development kit (R&D Systems, ref. DY1449), according to the manufacturer's instructions (antibody specific for MMP9/TIMP-1 complexes). The results are presented in FIG. 6.

Figure 6:
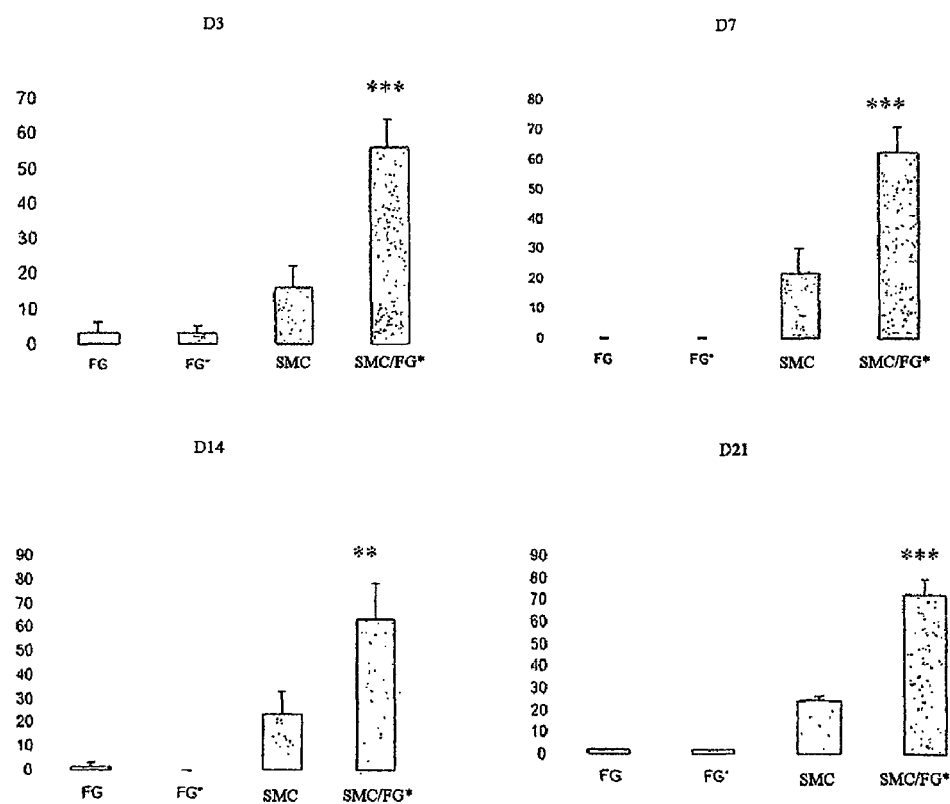
FIG. 6 depicts the results of ELISA assays that detect production of MMP9/TIMP-1 complexes in FG and/or SMC containing cell cultures.

Legend of FIG. 6:
X-axis
FG=culture of $10^5$ nonlabeled FGs;
FG*=culture of $10^5$ labeled FGs;
SMC=culture of $10^5$ SMCs;
SMC/FG*=coculture of $10^5$ labeled FGs and $10^5$ SMCs.
Y-axis=secretion of MMP9/TIMP-1 (pg/ml/$10^5$ cells)
**=Fischer Student's T test p<0.01
***=Fischer Student's T test p<0.001.

The results show that the amount of MMP9/TIMP-1 complexes assayed by ELISA is increased (×4) in the cocultures of SMCs and FGs (SMC/FG*). The same results are obtained at D3, D7, D14 and D21.

It follows from all these results that the decrease in MMP9 activity by the SMCs cocultured with the FGs does not come from a decrease in the synthesis of said MMP9, but from an increase in the synthesis of its inhibitor, TIMP-1, and therefore in inactive MMP9/TIMP-1 complexes.

Effects of the FG/SMC Cocultures on TGFβ Secretion

The cell interactions are studied through the expression of the cytokine TGFβ at D3, D7, D14 and D21/D28 (days of culture).

Evaluation of TGFβ Production by ELISA Assay

The TGFβ production was evaluated by ELISA assay using a DuoSet® ELISA Development kit (R&D Systems, ref. DY240), according to the manufacturer's instructions. The results of the ELISA assay at D3, D7, D14 and D21 are represented in FIG. 7.

Figure 7:
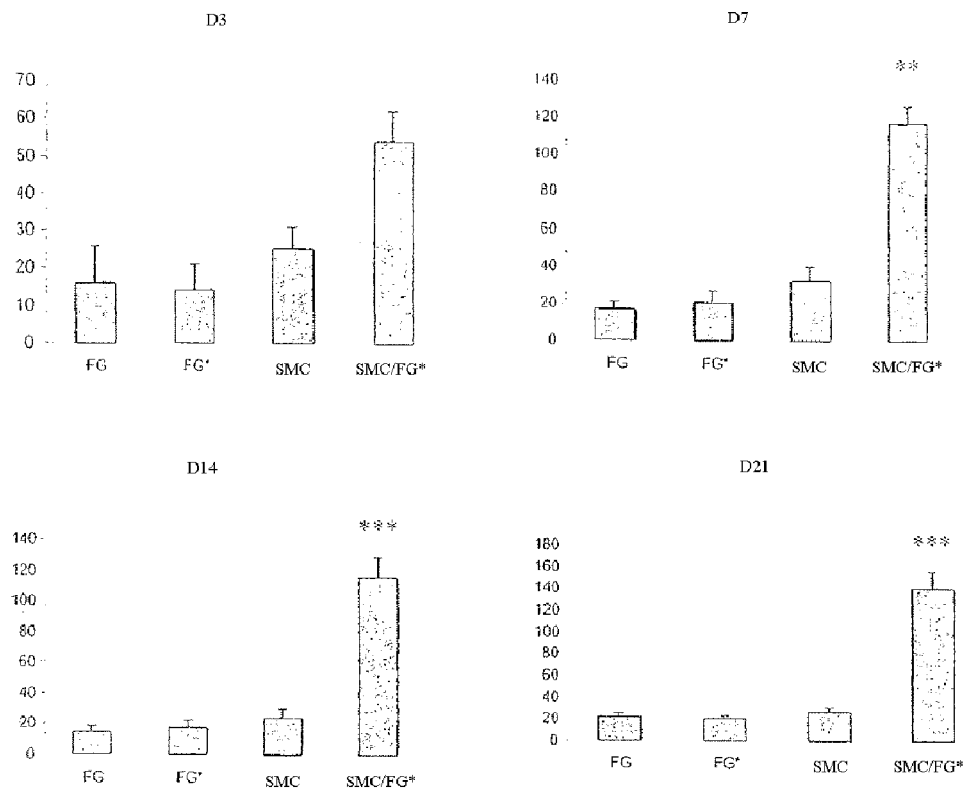
FIG. 7 depicts the results of ELISA assays that detect production of TGFβ in FG and/or SMC containing cell cultures.

Legend of FIG. 7:
X-axis
FG=culture of $10^5$ nonlabeled FGs;
FG*=culture of $10^5$ labeled FGs;
SMC=culture of $10^5$ SMCs;
SMC/FG*=coculture of $10^5$ labeled FGs and $10^5$ SMCs.
Y-axis=secretion of TGFβ (pg/ml/$10^5$ cells)
**=Fischer Student's T test p<0.01
***=Fischer Student's T test p<0.001.

Evaluation of TGFβ Production by Dot-Blot

The TGFβ production was evaluated by dot-blot, using a mouse anti-TGFβ1 monoclonal antibody (R&D Systems, ref. MAB 240), and using the protocol described above in the case of TIMP-1. The results obtained by dot-blot at D3, D7, D14 and D28 are represented in FIG. 8.

Figure 8:
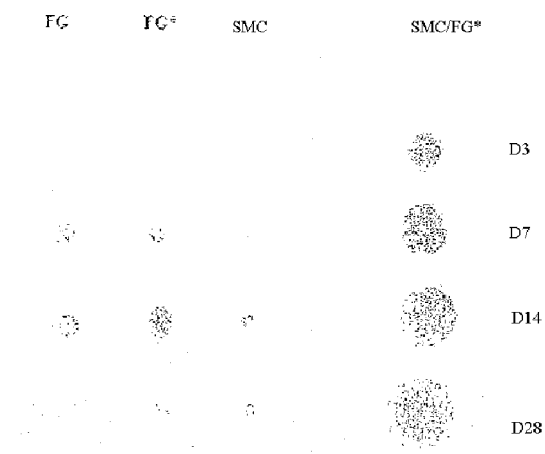
FIG. 8 depicts the secretion of TGFβ protein in the supernatant of FG and/or SMC cell cultures, as determined by dot-blot assay.

Legend of FIG. 8:
FG=culture of $10^5$ nonlabeled FGs;
FG*=culture of $10^5$ labeled FGs;
SMC=culture of $10^5$ SMCs;
SMC/FG*=coculture of $10^5$ labeled FGs and $10^5$ SMCs.

The results show the potentiation of the TGFβ secretion by the FG and SMC cells in coculture.

EXAMPLE 2

Comparison of the Effects of the Gingival Fibroblasts with Those of Dermal or Adventitial Fibroblasts on the MMP2 or MMP2 Activity of SMCs Cocultures of dermal fibroblasts (FDs) or adventitial fibroblasts (FAs) and of smooth muscle cells (SMCs) are carried out in a collagen gel, using the same protocol as that described in Example 1 above for the gingival fibroblasts.

The cells are obtained from skin samples for the dermal fibroblasts, from samples of adventitia for the adventitial fibroblasts, and from samples of arterial media for the smooth muscle cells.

Dermal or adventitial fibroblast cultures and smooth muscle cell cultures are carried out separately, as a control, under the same conditions.

Figure 9:
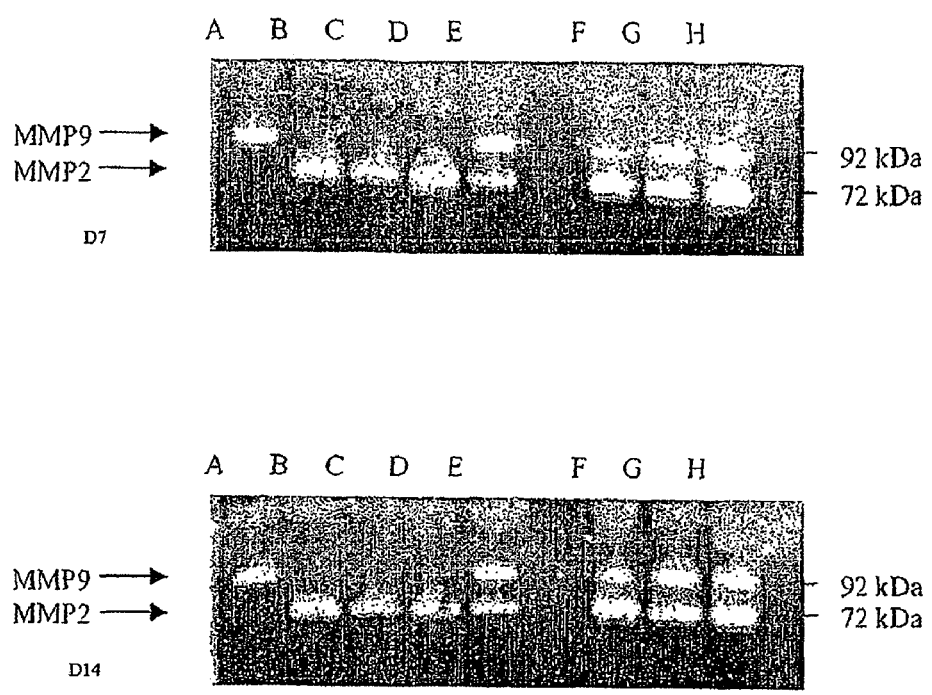
FIG. 9 depicts the activity of MMP9 and MMP2 as determined by zymography of samples of FG, FD, FA, and SMC containing cell cultures and cocultures of FG, FD, or FA cells with SMC cells.
Figure 10A:
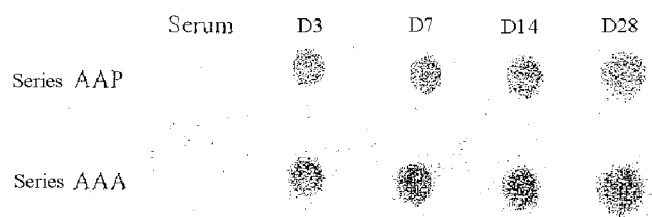
FIG. 10 depicts the expression of MMP1, MMP2, MMP3, TIMP-1 and TIMP-2 protein secreted into the medium of organotypic cultures of AAA and AAP arteries, as determined by dot-blot assay.
Figure 10B:
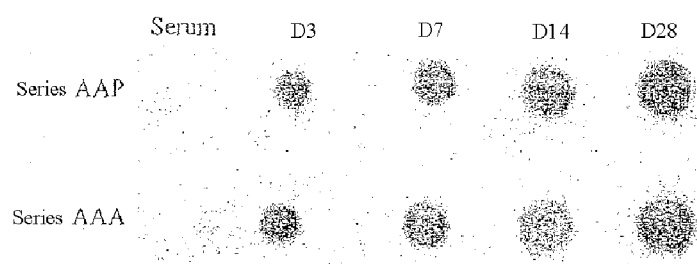
Figure 10C:
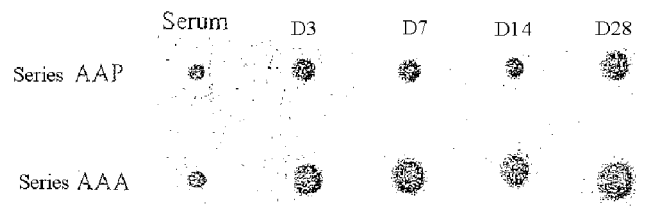
Figure 10D:
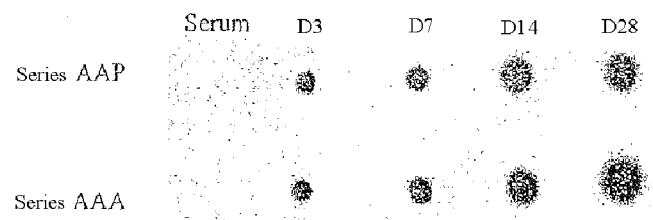
Figure 10E:
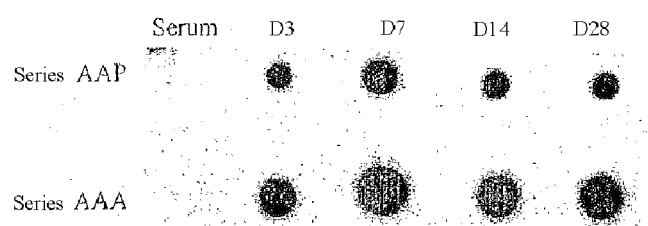

The cell interactions are studied at D7 and D14 by determination of the activities of MMP2 and of MMP9, secreted into the culture medium, by zymography as described in Example 1 above. In parallel, 20 µl of recombinant MMP9 (R&D Systems, ref. 911-MP) are subjected to the same electrophoresis in order to verify the type of MMP analyzed. The results are presented in FIG. 9.

A: 20 µl control (100 µg/ml) of recombinant MMP9;
B: MMP2 activity for 600 FGs cultured in a collagen gel;
C: MMP2 activity for 600 FDs cultured in a collagen gel;
D: MMP2 activity for 600 FAs cultured in a collagen gel;
E: MMP2 and MMP9 activities for 600 SMCs cultured in a collagen gel;
F: MMP2 and MMP9 activities for 600 SMCs and 600 FGs cocultured in a collagen gel;
G: MMP2 and MMP9 activities for 600 SMCs and 600 FDs cocultured in a collagen gel;
H: MMP2 and MMP9 activities for 600 SMCs and 600 FAs cocultured in a collagen gel.

The results show that, like the gingival fibroblasts (B), and unlike the SMCs (E), the dermal and adventitial fibroblasts in culture do not express MMP9 (C and D). On the other hand, the dermal and adventitial fibroblasts do not affect the activity of MMP9 secreted by the SMCs in coculture (G and H), unlike the gingival fibroblasts, which inhibit this activity (F). The same results are observed at D7 and D14. As regards MMP2, no significant modification of the activity of the free forms of this enzyme is observed. The gingival fibroblasts, like the dermal or adventitial fibroblasts, do not appear to modify the secretion of MMP2 in coculture with the SMCs.

EXAMPLE 3

Organotypic Cultures of Lesioned Arteries

The three-dimensional culture of lesioned arteries in collagen gel was developed by the inventors in order to provide a model for analyzing arterial remodeling over time.

Obtaining the Cultures

Atherosclerotic lesions are induced in 5 New Zealand white rabbits by means of the combination of air desiccation and a high-cholesterol diet, as described by LAFONT et al. (Circ. Res. 76(6): 996-1002, 1995; Circulation 100(10): 1109-1115, 1999). After 4 weeks, the presence of atherosclerotic lesions is confirmed by arteriography inside the two femoral arteries. Iatrogenic lesions are then produced on the left femoral arteries using an angioplasty balloon catheter (3 insufflations at 6 atm for 60 sec).

24 hours after the angioplasty, the rabbits are sacrificed by intracardiac injection of Phenobarbital. The arteries are collected after dissection and stored in DMEM containing 20% FCS, at 4° C., for 3-10 hours, before placing in culture. In this way, 5 progressive atherosclerotic arteries (AAPs) and 5 atherosclerotic arteries 24 hours after angioplasty (AAAs) are collected.

The arteries are rinsed with a Hanks solution and then dissected so as to conserve the adventitia and eliminate the surrounding tissues. Finally, each artery is broken down into 4 segments of 5-7 mm.

Each segment is placed in a 10 ml Erlenmeyer flask containing 6 ml of culture medium (DMEM/20% FCS, usual antibiotics and antifungals), 3.4 ml of rat collagen type I (Jacques Boy Institut, REIMS, France), and 600 µl of filtered 0.1 N NaOH, and homogenized with the solution. Finally, the entire mixture is transferred into a culture dish, in an incubator at 37° C./5% $CO_2$. Each week, 1 ml of culture medium is added to the supernatant in order to compensate for evaporation.

At D3, D7, D14 or D28 (days of culture), the arteries and their collagen networks are recovered, rinsed with 1× PBS, and fixed in a solution of PBS/4% paraformaldehyde for 48 hours. They are then dehydrated in 70°, 95° and then 100° alcohol, and finally in toluene, before being embedded in paraffin. The paraffin blocks are prepared with a view to cutting sections.

The culture supernatants of the 5 series of arteries are stored at −80° C.

Morphometric Evaluation of the Cultures

Sections 7 µm thick are cut on a microtome, and then stained using three different specific protocols:

Hemalaun-eosin protocol: after rehydration, the sections are covered with hemalaun for 5 min before differentiation with tap water, and then with eosin for 1 min. The microscope preparations are finally rinsed with distilled water before dehydration and final assembly.

Sirius red protocol: after rehydration, the sections are covered with Sirius red for 30 min. The microscope preparations are finally rinsed with distilled water before dehydration and final assembly.

Catechin(+)-fuchsin protocol: after partial rehydration (stopped at 95° alcohol), the sections are immersed in a staining solution, in the dark, for 2½ hours. A rapid rinse with 95° alcohol (with 2 drops of hydrochloric acid) is performed before dehydration and final assembly.

Cell Counting

The hemalaun-eosin-stained sections are observed under a microscope coupled to a computer (BIOCOM 200 station). The semi-automatic counting of the cells is made possible by marking off the nuclei. The results are given as number of cells per unit of surface area.

Within the intimal (AAP) and neointimal (AAA) proliferations, the number of cells per unit of surface area significantly decreases over time. This reduction is very significant between D3 and D7 ($p<0.001$), significant between D7 and D14 ($p<0.01$) and rather significant between D14 and D28 ($p<0.05$).

Within the media, the number of smooth muscle cells is relatively stable, both in the case of the AAPs and the AAAs.

Within the collagen network, the number of cells per unit of surface area increases. This increase is very significant between D3 and D7 ($p<0.001$), and significant between D7 and D14 ($p<0.01$). This increase is no longer significant between D14 and D28: a threshold effect appears to intervene at D28.

Arterial Morphology

With the same image digitization process, measurements of the thickness of the media and measurements of the thickness of the intimal proliferations (AAPs) and of the neointimal proliferations (AAAs) are carried out. The measurements are taken 10-12 times, in 6 different areas inside each artery in culture.

These measurements do not show any significant modifications over time.

Quantification of the Extracellular Matrix Components
Collagen Network Components After image digitization, the software can evaluate the relative surface area of the collagen component (on sections stained with Sirius red, observed under polarized light so as to reveal the fibrillar collagens).

The collagen network components are evaluated in the intimal proliferations (AAPs) and the neointimal proliferations (AAAs). In the two cases, an increase in the density of the collagen network is observed over time. In addition, since the measurements are carried out on sections observed under polarized light, the increase observed concerns the fibrillar component of the collagen network.

Elastic Network Components

After image digitization, the software can evaluate the relative surface area of the elastic networks (on sections stained with catechin(+)-fuchsin).

The relative surface area of the elastic network components in the media shows a reduction over time. In the case of the AAPs, the reduction is significant between D3 and D14 ($p<0.01$) and very significant between D14 and D28. In the case of the AAAs, this reduction is significant only between D14 and D28 ($p<0.06$). However, the AAPs initially (at D3) have a more significant elastic component than the AAAS. However, at D28, the elastic network components are substantially equivalent between these two series of arteries.

Finally, in the intimal and neointimal proliferations, an increase in the elastic network components is observed over time. This increase is very significant between D7 and D28 for the AAPs, and between D14 and D28 for the AAAs ($p<0.001$).

Elastic Fiber Fragmentation

The sections stained with hemalaun-eosin are observed by electromicroscopy under UV. After the sections have been photographed and the photographs have been studied by computer, the length of the elastic fibers between two fragmentation points is measured. This length reflects the state of fragmentation: the shorter the length of the fibers, the more significant the fragmentation.

In the AAPs, the elastic laminae are well-organized, parallel to one another and concentric at D3. The fiber fragmentation is therefore very moderate. However, the length of the elastic fibers decreases over time. This reduction is very significant between D3 and D7, and D14 and D28 ($p<0.001$). This reflects the progressive fragmentation of the elastic fibers, which appear to be disorganized and fragmented at D28.

In the AAAs, the elastic laminae are disorganized and fragmented from the first days of culture. This fragmentation at D3 is similar to what is observed for the AAPs at D28. However, this fragmentation phenomenon continues to develop over time and as significantly as in the case of the AAPs. In this model, the UV-microscopy result shows that the length of the elastic fibers in the lesioned arteries decreases from 466 µm at D3 to 87 µm at D28.

All the morphometric analyses show that the arterial tissue coherence in culture is maintained to the end of the experimental period. In addition, the dynamic cellular matrix remodeling phenomena observed in vitro correspond to the data established in vivo, both in violent (AAA) or slow (AAP) inflammatory situations. It therefore appears that the organotypic cultures of lesioned arteries in collagen gel constitute a valid ex vivo aneurism model.

EXAMPLE 4

Evaluation of the Secretion of Key Enzymes of Arterial Remodeling by the Organotypic Cultures of Lesioned Arteries Secretion of MMP-1, -2 and -3, and TIMP-1 and -2

The expression of MMP1, MMP2, MMP3, TIMP-1 and TIMP-2 secreted into the medium for organotypic culture of AAA and AAP arteries is analyzed by dot-blot as described in Example 1 above, using human antibodies directed against these MMPs and TIMPs (Valbiotech). As a control, the presence of these MMPs and TIMPs is also investigated in the culture serum (FCS). The results are presented in FIG. 10.
A: MMP1 expression
B: MMP3 expression
C: MMP2 expression
D: TIMP-1 expression
E: TIMP-2 expression.

Between D3 and D28, the results show:
- a significant increase in the expression of MMP-1 (A) and MMP-3 (B), with a significantly higher concentration in the AAA cultures than in the AAP cultures. MMP1 and MMP3 are absent from the culture serum;
- an increase in the expression of MMP2 (C) over the first week (D7) and a decrease over the second week (D14), then a new increase which reaches its maximum at D28. The same phenomenon is observed in the two types of arterial cultures, although MMP2 remains considerably more expressed after angioplasty (AAA) than in the AAP cultures. In addition, the MMP2 concentrations are very significantly lower in the serum than in the culture supernatants;
- a gradual increase in the expression of TIMP-1 (D) over the first two weeks, without significant differences between the two series of arterial cultures. On the other hand, over the next two weeks, the AAA cultures exhibit a peak of TIMP-1, whereas the expression of the enzyme stagnates in the AAP cultures. TIMP-1 is absent from the culture serum;
- an increase in expression of TIMP-2 (E) in the first week, before stagnation at levels that are much lower in the AAP cultures. After angioplasty, a peak of TIMP-2 expression is also observed in the first week before stagnation at very high concentrations. In addition, TIMP-2 remains much more highly expressed after angioplasty than in the AAP cultures. TIMP-2 is absent from the culture serum.

Production of MMP9

The expression of MMP2 and MMP9, secreted into the medium for organotypic culture of AAA and AAP arteries, is analyzed.

Evaluation of the Activity of MMP9 by Gelatin Zymography

Figure 11:
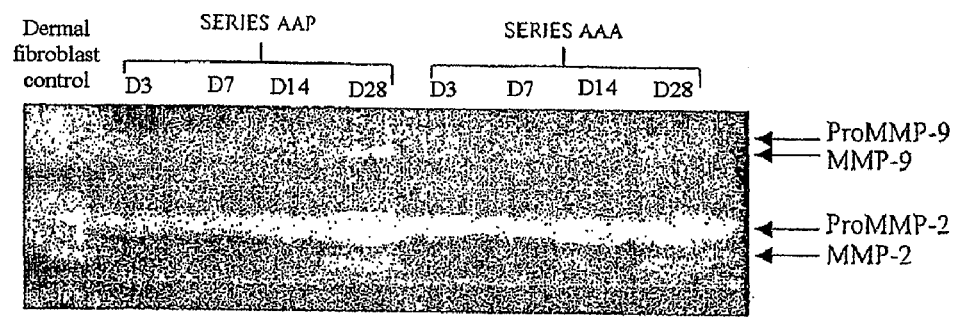
FIG. 11 depicts the activity of MMP9 and MMP2 in the supernatant of organotypic cultures of AAA and AAP arteries, as determined by gelatin zymography.

70 µl of arterial (AAP and AAA) organotypic culture supernatant are diluted to ⅗ in 1 M Tris at pH 6.8, containing 50% of glycerol and 0.4% of bromophenol blue, and then subjected to electrophoresis in an SDS 10% polyacrylamide gel containing 1 mg/ml of pig skin gelatin (Sigma, ref. G2500) in a Laemmli buffer solution, at 4° C., at 80 volts in the stacking gel and then 180 volts in the separating gel. After migration, the gels are washed in 2.5% Triton X-100 (twice 30 min at ambient temperature), and then incubated in a saline buffer solution, at 37° C., for 48hours. The gels are then stained with 0.25% Coomassie blue (Biorad, ref. R250) and then destained; the bands of enzymatic activity appear translucent, as shown in FIG. 11.

Computerized morphometric analysis makes it possible to quantify the gelatinolytic activities revealed by zymography. The image of the gel is transmitted to the computer using a video camera. The software (Imagenia 3000, BIOCOM 200 station) converts the intensity of the enzymatic bands into levels of gray: the higher the intensity of the band, the higher the level of gray. An absence of lysis corresponds to the level of gray 0, maximum lysis corresponds to the level of gray 255. The band surface area is measured semi-automatically by a definition of the outline. The quantification, in arbitrary units U, is obtained by multiplying the surface area S of the band by the level of gray.

The results show a gradual and significant increase in the enzymatic activity of MMP2 and MMP9 between D3 and D28, and which appears to be more significant after angioplasty (AAA) than in the AAP cultures.

Evaluation of MMP9 Expression by Dot-Blot

Figure 12:
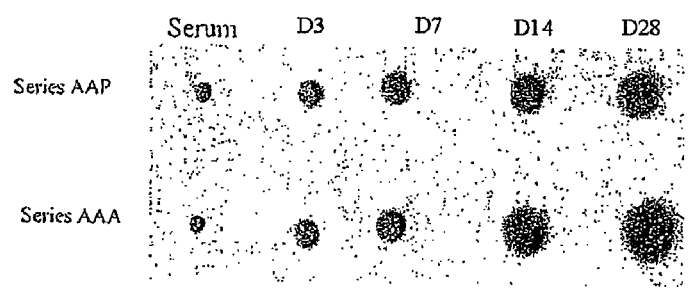
FIG. 12 depicts the expression of MMP9 protein in organotypic cultures of AAA and AAP arteries, as determined by dot-blot assay.
Figure 13A:
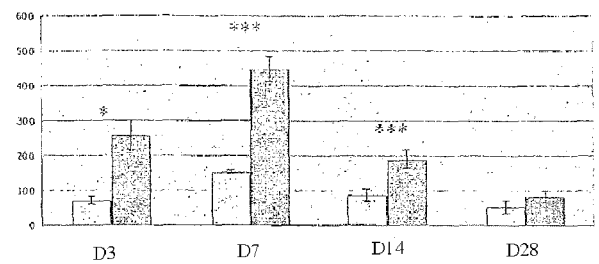
FIG. 13 depicts the results of ELISA assays that detect IL-1β (FIG. 13A), IL-6 (FIG. 13B), IL-4 (FIG. 13C), and TGFβ (FIG. 13D) secreted into the supernatant of AAA and AAP arterial cultures.
Figure 13B:
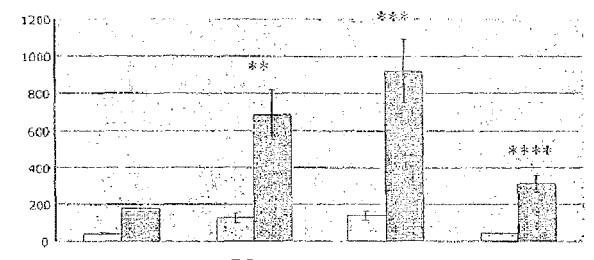
Figure 13C:
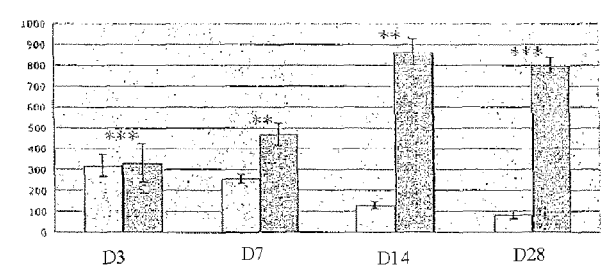
Figure 13D:
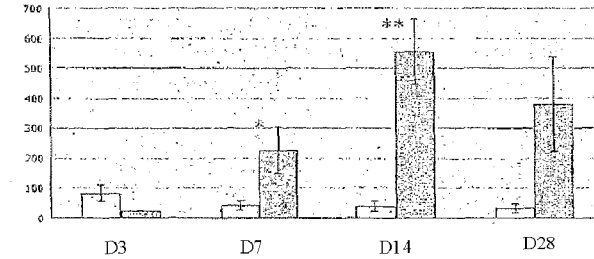

The dot-blot is carried out as described in Example 1 above, using a human antibody directed against MMP9 (Valbiotech). As a control, the presence of MMP is also investigated in the culture serum (FCS). The results are presented in FIG. 12.

The results show a very significant increase in MMP9 between D3 and D28 in the case of both the AAP cultures and the AAA cultures (ratio of 1 to 4). In addition, from D14, the MMP9 expression by AAA cultures is significantly greater than that of the AAP cultures. The culture serum contains a small amount of MMP9, but this amount remains significantly lower than the concentrations measured in the arterial organotypic culture supernatants.

Cytokine Secretion

The cytokines IL-1β, IL-4, IL-6 and TGFβ are quantified in the supernatant of arterial cultures at D3, D7, D14 and D28, by ELISA assay as described in Example 1 above, using, respectively, the Quantikine® (R&D Systems, ref. DLB50) and DuoSet® ELISA Development (R&D Systems, ref. DY204, ref. DY206 and DY240) kits. The mean values obtained are transferred into the form of histograms and analyzed statistically. The results are presented in FIG. 13.

X-axis
A: quantification of IL-1β;
B: quantification of IL-6;
C: quantification of IL-4;
D: quantification of TGFβ;
Y-axis=pg/ml of cytokines secreted per 24 hours
□=culture of AAP arteries
■=culture of AAA arteries (=after angioplasty)
*=Fischer Student's T test p<0.05
**=Fischer Student's T test p<0.02
***=Fischer Student's T test p<0.01
****=Fischer Student's T test p<0.001.

The results show:
- an IL-1β secretion peak at D7, before an abrupt decrease (A). This phenomenon is 4 times greater after angioplasty than in the AAP cultures;
- an IL-6 secretion peak which is later (B) in comparison with that of IL-1β, but AAP/AAA ratios that are very similar to those of IL-1β. The functional coordination between IL-1β and IL-6 is thus once again confirmed by the correlation of their secretion profile;
- starting from identical values at D3, a significant decrease in IL-4 levels (C) in the AAP cultures (level: 3) and a proportionally identical increase in IL-4 levels after angioplasty (level x3);
- a very significant increase in TGFβ secretion (D) in the AAP cultures (level: 2), but a very substantial increase after angioplasty (factor of 20 between D3 and D14).

Indirect Immunodetections of MMP9 and MMP3

Sections 7 μm thick of AAA and AAP cultures at D3 and D28 are rehydrated (two toluene baths followed by 100° and 95° alcohol solutions) and then treated for 2 min with 0.2% pepsin (Sigma) diluted in acetic acid (⅒). The microscope preparations are rinsed in 0.1 M PBS, pH 7.2, for 10 min, and then PBS-1% glycine, for 30 min. The two rinses are carried out in 1× PBS.

The sections are then covered with a blocking solution (1% BSA, PBS-0.05% Tween, and 10% horse serum) for 30 min at 37° C.

The blocking solution is removed and replaced with a primary antibody diluted in a solution containing 1% BSA and PBS-0.05% Tween: 1/50 anti-MMP3 or anti-MMP9 [Oncogène (Merk Eurolab)]. The sections are covered with the primary antibody overnight at ambient temperature.

The microscope preparations are rinsed 3×10 min in 1× PBS. The sections are then covered with a specific biotinylated secondary antibody for 90 min (Vector Vectastain® kit (ABC kit) Biovalley, Elite PK-6102). The microscope preparations are rinsed 3× in 1× PBS.

The endogenous peroxidases are blocked by adding hydrogen peroxide to the sections for 20 min at 37° C. The microscope preparations are rinsed twice in 1× PBS and once in PBS-3% NaCl. The avidin-biotin complex is prepared and deposited onto the sections for 45 min at ambient temperature. The microscope preparations are rinsed twice in PBS-3% NaCl and then 0.1 M Tris-HCl, pH 7.6.

The final development is carried out with DAB (DiAminoBenzidine) on each section.

Contrast staining with hemalaun is carried out in order to improve the contrast between the peroxidase immunolabeling and the cell bodies.

The sections are finally dehydrated with two successive baths of alcohol (95° and 100°) followed by two toluene baths. The microscope preparations are mounted with DEPEX (GURR®).

In the AAP cultures, MMP3 and MMP9 appear diffusely in the media at D3 before becoming concentrated along the internal elastic lamina at D14, and invading the intima. At D3, the MMP3 labeling is much more intense than the MMP9 labeling; however, the opposite phenomenon gradually develops and, at D28, the MMP9 labeling is very intense in the media and especially in the intima, whereas it remains moderate for MMP3.

In the AAA cultures, the MMP9 dispersion appears intensely along the internal elastic lamina at D3, before migrating into the middle area of the neointima, so as to finally extend diffusely within the entire media. The distribution of MMP3 exhibits clearly more moderate kinetics: at D3, its presence is still diffuse in the media, and it is only at D7 that the dispersion of MMP3 accumulates along the internal elastic lamina, before migrating into the middle area of the neointima at D14, and extending over the entire neointima at D28. However, the MMP3 labeling always remains less intense than that of MMP9.

These results from immunohistochemistry on microscope preparations of arterial cultures between D3 and D28 make it possible to confirm a correlation between the increase in elastic fiber fragmentation and the increase in MMP9 secretion.

EXAMPLE 5

Effects of Cocultures of Arteries and Gingival Fibroblasts on the Production of MMP9 and of TIMP-1 and on the Elastic Network Obtaining Cocultures of Arteries and Gingival Fibroblasts Sections of lesioned arteries from rabbit (atherosclerotic rabbit AAP) obtained as described in Example 3 above are cultured in the presence of gingival fibroblasts under the following conditions: 100 000 autologous gingival fibroblasts, taken from a rabbit 1 month before the latter is sacrificed for the artery/FG cocultures, are mixed with the collagen gel before it is polymerized, then the 2 mm (approximately 3 mg) arterial fragment is deposited in the middle of the gel. The culture techniques are described in Examples 1 and 3 above.

Effects of FG/Artery Interactions on MMP9 and TIMP-1 Expression

The cell interactions are studied between D3 and D21 (days of culture) through the expression of MMP9 and TIMP- 1, secreted into the artery and FG coculture medium. As a control, the expression of these enzymes is also analyzed in cultures of FGs alone and in arterial organotypic cultures, carried out under the same conditions as those described respectively in Examples 1 and 3 above.

Evaluation of the Activity of MMP2 and MMP9 by Zymography

Figure 14:
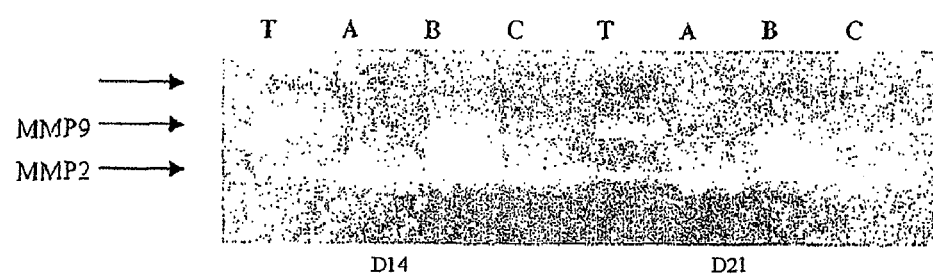
FIG. 14 depicts the activity of MMP9 and MMP2 secreted by FG cells cultured in a collagen gel, arteries cultured in a collagen gel, and the combination of FG cells and arteries cocultured in a collagen gel.

The expression of MMP2 and MMP9 secreted into the supernatant from cocultures of arteries and FGs at D14 and D21 is analyzed by gelatin zymography. The results are presented in FIG. 14.

T: 10 μl standard (100 μg/ml) of recombinant MMP9 (R&D Systems, ref. 911-MP) and of recombinant MMP2 (R&D Systems, ref. 902-MP);
A: cell culture of 100 000 FGs in a collagen gel;
B: culture of arteries in a collagen gel;
C: cocultures of arteries and 100 000 FGs in a collagen gel.

The results show that the gingival fibroblasts in culture do not express MMP9 (A and D), unlike the organotypic cultures of arteries (B and E). On the other hand, the gingival fibroblasts inhibit the secretion of MMP9 by the arteries in coculture (C and F). The same results are observed at D14 and D21. As regards MMP2, no significant modification of the activity of the free forms of this enzyme is observed. The gingival fibroblasts do not appear to modify the secretion of MMP2 in coculture with the arteries.

Evaluation of MMP9 and TIMP-1 Expression by Dot-Blot

The dot-blot analysis of the supernatant from cocultures of arteries and gingival fibroblasts between D3 and D21 is carried out as described in Example 1 above, using anti-MMP9 and anti-TIMP-1 antibodies. The MMP9 secretion and TIMP-1 secretion results are presented, respectively, in FIGS. 15 (A=dot-blot, B=quantification of the dot-blot) and 16 (A=dot-blot, B=quantification of the dot-blot).

X-axis
T=control (10 pg of recombinant MMP9, R&D Systems, ref. 911-MP);
FG=culture of 100 000 gingival fibroblasts in a collagen gel;
A=organotypic culture of arteries in a collagen gel;
A/FG=coculture of arteries and 100 000 gingival fibroblasts in a collagen gel.
Y-axis=secretion of MMP9 (in pg).

Figure 15:
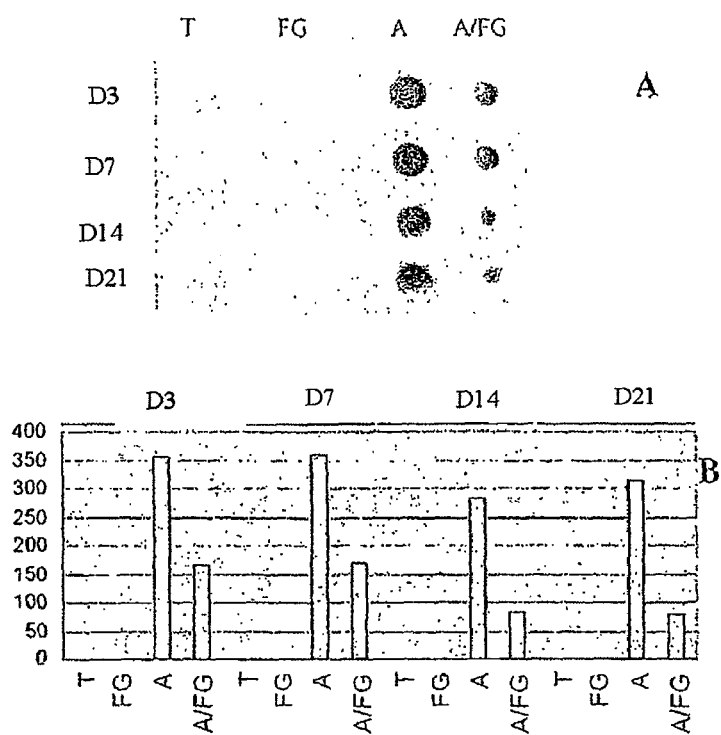
FIG. 15A depicts the expression of MMP9 protein secreted into the supernatant of cocultured FG cells and arteries, as determined by dot-blot assay. Quantification of the results shown in FIG. 15A is presented in FIG. 15B.
Figure 16:
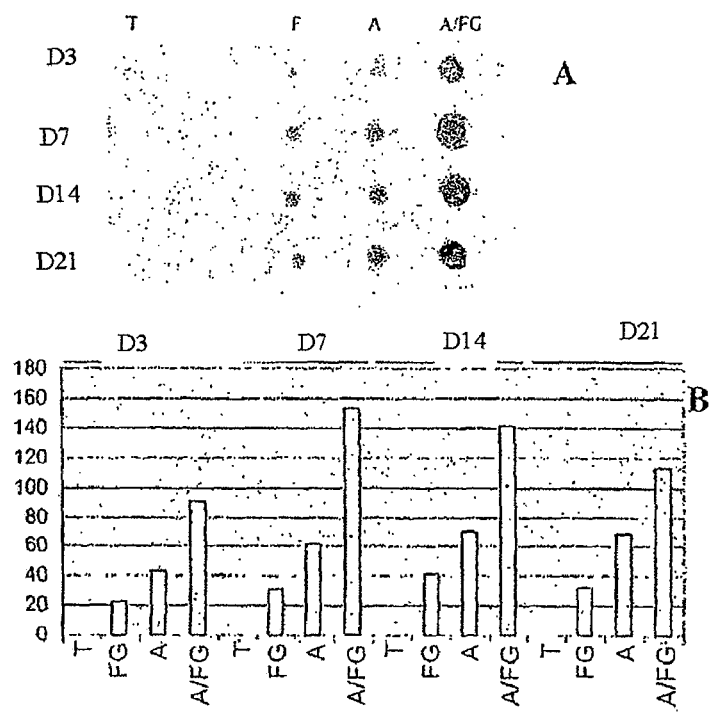
FIG. 16A depicts the expression of TIMP-1 protein secreted into the supernatant of cocultured FG cells and arteries, as determined by dot-blot assay. Quantification of the results shown in FIG. 16A is presented in FIG. 16B.

The results show that the gingival fibroblasts inhibit the secretion of MMP9 in the cocultures of arteries and FGs between D3 and D21 (FIG. 15). In parallel, a large increase in the secretion of TIMP-1 is observed in the A/FG cocultures in comparison with that detected in the separate FG and A cultures (FIG. 16). The same results are obtained at D3, D7, D14 and D21.

Evaluation of the Transcription of MMP9 and TIMP-1 by RT PCR

The extraction of the MMP9 mRNA and the TIMP-1 mRNA from cocultures of arteries and gingival fibroblasts at D14, and the RT PCR analysis, are carried out as described in Example 1 above, using primers specific for MMP9 and for TIMP-1. The MMP9 and TIMP-1 transcription analysis results are presented in FIGS. 17 and 18, respectively.

S: DNA molecular weight standard (Multiplex PCR© kit, BioSource International);
G: collagen gel alone;
FG: FG cell culture (1 μg RNA);
A: organotypic culture of arteries (1 μg RNA);
A/FG: coculture of arteries and FGs (1 μg RNA).

Figure 17:
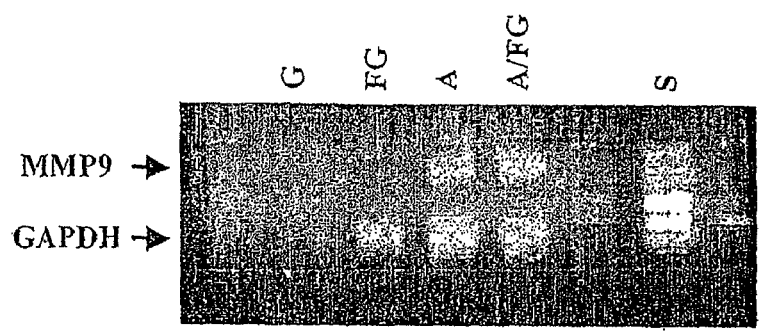
FIG. 17 depicts expression of MMP9 mRNA in cocultured FG cells and arteries, as determined by RT-PCR using MMP9 primers.
Figure 18:
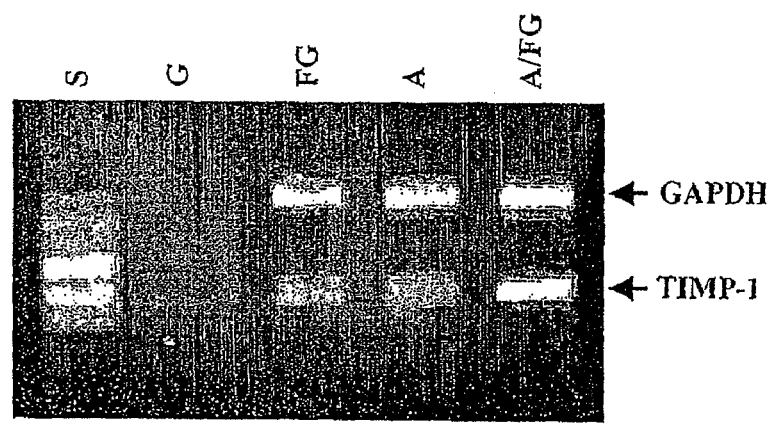
FIG. 18 depicts expression of TIMP-1 mRNA in cocultured FG cells and arteries, as determined by RT-PCR using TIMP-1 primers.

The results show no transcriptional modification of MMP9 in the cultures of arteries and the cocultures of arteries and FGs (FIG. 17). On the other hand, an increase in TIMP-1 transcription is observed in the cocultures of arteries and FGs in comparison with that observed in the cultures of FGs or of arteries (FIG. 18), which correlates with the increase in TIMP-1 secretion (FIG. 16).

Quantification of MMP9/TIMP-1 Complexes

Figure 19:
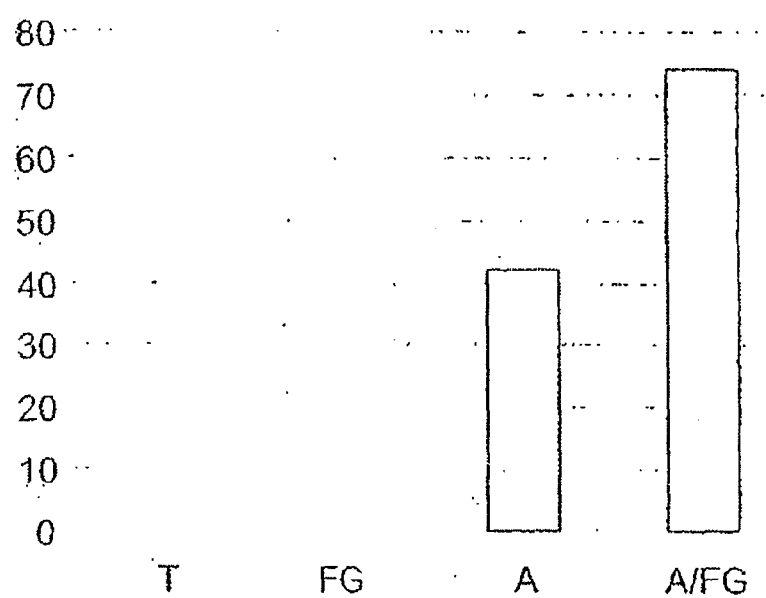
FIG. 19 depicts the results of ELISA assays that detect production of MMP9/TIMP-1 complexes in cocultures of FG cells and arteries.

The quantification of the expression of MMP9/TIMP-1 complexes in the cocultures of arteries and gingival fibroblasts at D14 is carried out by ELISA assay as described in Example 1 above. The results are presented in FIG. 19.

X-axis
T=control (collagen gel alone)
FG=culture of 100 000 gingival fibroblasts in a collagen gel
A=organotypic culture of arteries in a collagen gel
A/FG=coculture of arteries and gingival fibroblasts
Y-axis=secretion of MMP9/TIMP-1 complexes (pg/ml).

The results show that the amount of MMP9/TIMP-1 complexes is increased in the cocultures of arteries and FGs ($\times 1.8$).

All the biochemical results show that the gingival fibroblasts in coculture with arteries inhibit the activity of MMP9 secreted by arterial SMCs, not by decreasing the synthesis of the enzyme, but by inducing an increase in the synthesis of TIMP-1 and the formation of inactive MMP9/TIMP-1 complexes, regardless of the culture time (from D3 to D21). These ex vivo results therefore confirm those observed in vitro (Example 1 above).

Analysis of the Elastic Network

Figure 20:
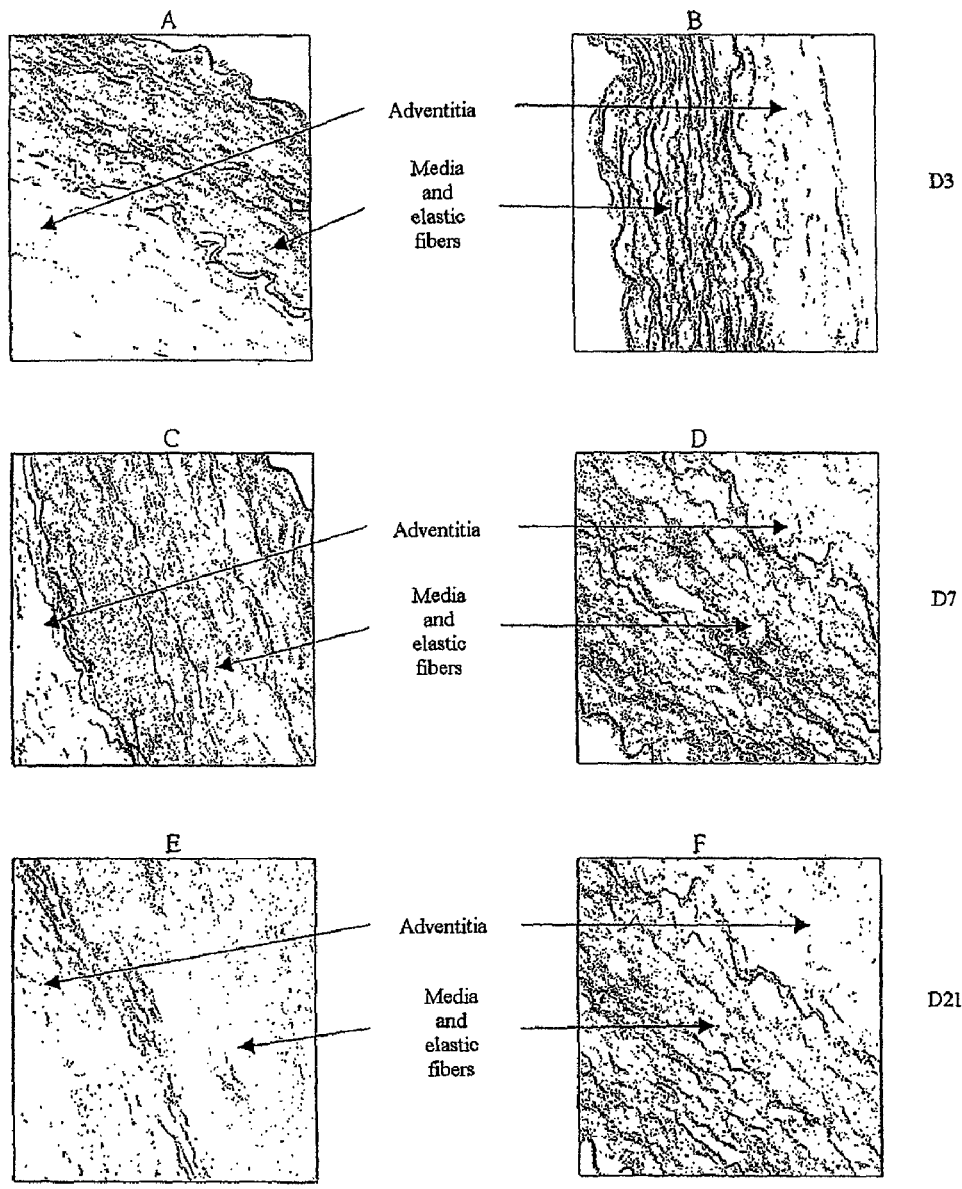
FIG. 20 depicts 7 mm sections of lesioned arteries cultured alone or cocultured with gingival fibroblasts, following orcein staining and microscopic (40×) observation.

Sections of 7 μm originating from lesioned arteries cocultured with gingival fibroblasts for 3, 7 and 14 days are observed under the microscope ($\times 40$) after orcein staining. As a control, sections of arteries cultured alone as described in Example 3 above are analyzed, under the same conditions. The results are presented in FIG. 20.

At D3
A: artery cultured alone
B: artery cocultured with gingival fibroblasts
At D7
C: artery cultured alone
D: artery cocultured with gingival fibroblasts
At D21
E: artery cultured alone
F: artery cocultured with gingival fibroblasts.

In the arteries cultured alone, a shortening and a gradual disappearance of the elastic fibers is observed over time (A, C and E), whereas in those cocultured with FGs, the elastic network remains dense (B, D and F). The results therefore show that there is a protection of the elastic network over time when the arteries are cultured in the presence of gingival fibroblasts.

It follows from this study that the conservation of the integrity of the elastic network of the media is correlated with a decrease in MMP9 activity subsequent to an increase in TIMP-1. The gingival fibroblast therefore appears to be a cell that can modify vascular remodeling, by reproducing, in the artery, its repair potential naturally expressed in the gum.

EXAMPLE 6

Transplantation of Human Gingival Fibroblasts In Vivo Into Rabbit Arteries

The objective of this study is to determine the feasibility of the injection and the validation of the labeling of the fibroblasts with nanoparticles, verified by Perl's staining. The human cells injected into the rabbit make it possible to visualize, by HLA immunodetection, whether the cells stained with Perl's are indeed the injected fibroblasts. This is because the nanoparticles could escape from dead FGs and label SMCs of the media.

The transplantation of human gingival fibroblasts is carried out in vivo in rabbit arteries in two different models: a normal artery model and an aneurism model (elastase model).

The human gingival fibroblasts are labeled in monolayer culture with the ferromagnetic nanoparticles, as described in Example 1 above, and then trypsinized.

Figure 21:
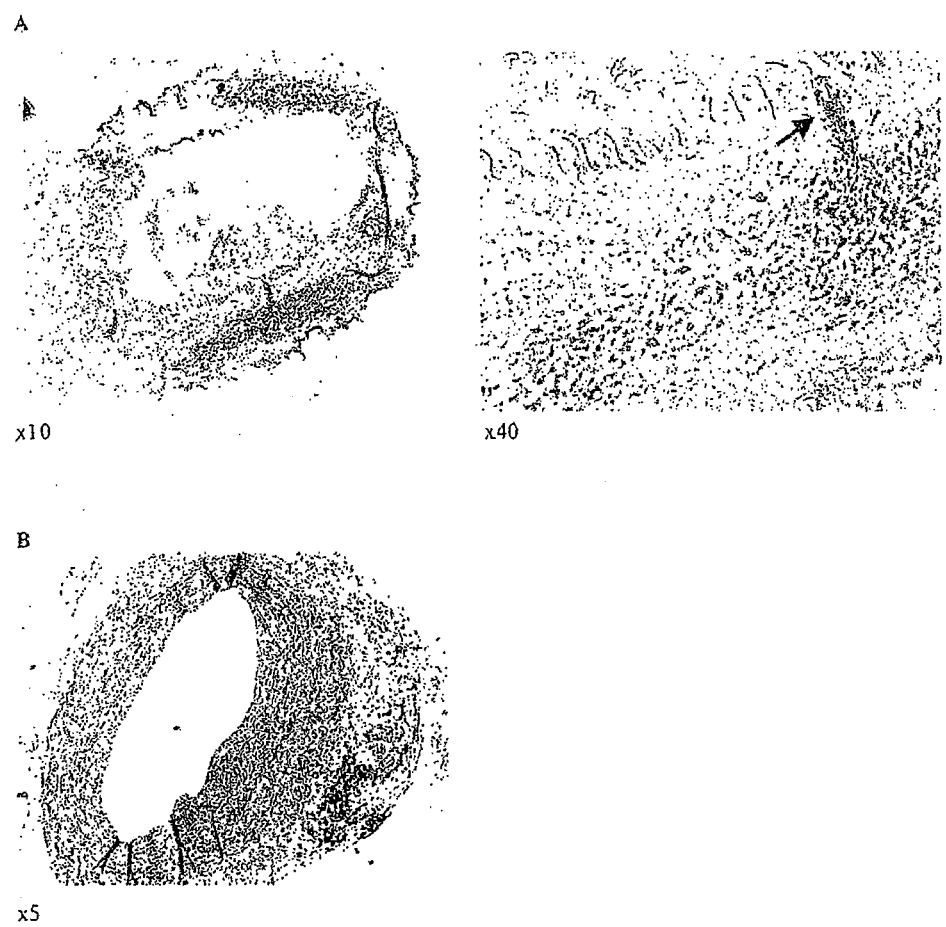
FIG. 21 depicts human gingival fibroblasts labeled with nanoparticles and injected into model rabbit arteries.

The transplantation procedure is identical to that described in Example 6 above. The results are presented in FIG. 21.

A: normal artery model (×10 and ×40)

B: aneurism model (×5).

The results show that there is a superposition between the anti-human HLA labeling and the Perl's staining (FIG. 21A), which confirms the validity of this injection technique. The cells have a normal morphology, and a site of penetration of the INFILTRATOR into the artery can be observed (cf. arrow FIG. 21A, ×40). FIG. 21B shows an injection of fibroblasts into an aneurysmal artery.

EXAMPLE 7

In Vivo Transplantation of Autologous Gingival Fibroblasts into Rabbit Arteries The gingival fibroblasts are labeled in monolayer culture with the ferromagnetic nanoparticles, as described in Example 1, and then trypsinized.

Figure 22:
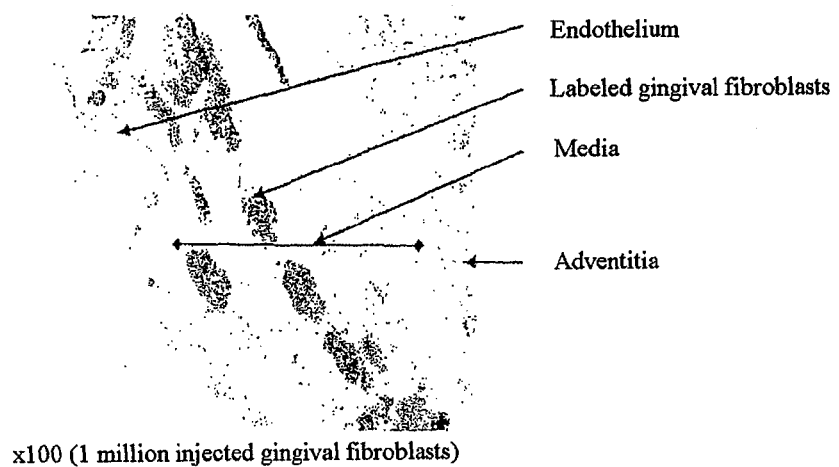
FIG. 22 depicts a section of a rabbit iliac artery following injection of human gingival fibroblasts labeled with nanoparticles.

They are injected at various amounts (from $10^5$ to $5 \times 10^6$ cells) into the rabbit iliac arteries using an INFILTRATOR catheter (Boston Scientific) (TEIGER et al., Eur. Heart J. 18: abstract suppl. 500, 1997). The rabbits are sacrificed 24 h after the injection and the injection sites are visualized. The results are presented in FIG. 22.

At high magnification (×100), the Perl's staining makes it possible to see the nanoparticles on the 6 μm histological sections. The injected fibroblasts are located in the media, and exhibit a normal morphology.

What is claimed is:

1. A method for treating an arterial-remodeling pathology, said pathology being selected from the group consisting of an aneurism and a post-angioplasty stenosis or restenosis, comprising obtaining fibroblasts from gingival tissue taken from an individual, culturing said gingival fibroblasts, and implanting said cultured gingival fibroblasts into the wall of a lesioned artery of said individual.

2. A method for treating an arterial-remodeling pathology in an individual suffering from an arterial-remodeling pathology involving an excessive activity of MMP9, said pathology being selected from the group consisting of an aneurism and post-angioplasty stenosis or restenosis, comprising obtaining fibroblasts from gingival tissue take from an individual, culturing said gingival fibroblasts, and implanting said cultured gingival fibroblasts into the wall of a lesioned artery of said individual.

3. A method for treating an arterial-remodeling pathology, wherein said method comprises implanting gingival fibroblasts into the wall of a lesioned artery, and wherein said pathology is an aneurism.

4. The method of claim 3, wherein said fibroblasts are derived from gingival tissue taken beforehand from the individual for whom the treatment is intended.

5. A method for treating an arterial-remodeling pathology, wherein said method comprises implanting gingival fibroblasts into the wall of a lesioned artery, and wherein said pathology is a post-angioplasty stenosis or restenosis.

6. The method of claim 5, wherein said fibroblasts are derived from gingival tissue taken beforehand from the individual for whom the treatment is intended.

* * * * *

UNITED STATES PATENT AND TRADEMARK OFFICE
CERTIFICATE OF CORRECTION

PATENT NO. : 8,119,122 B2  
APPLICATION NO. : 11/571542  
DATED : February 21, 2012  
INVENTOR(S) : Antoine Lafont and Bruno Gogly Page 1 of 1

It is certified that error appears in the above-identified patent and that said Letters Patent is hereby corrected as shown below:

At Column 8, line 49, delete "MMP2 Activity" and insert --MMP9 Activity--.

Signed and Sealed this
Twenty-fifth Day of September, 2012

David J. Kappos
*Director of the United States Patent and Trademark Office*